United States Patent [19]

Krapcho

[11] Patent Number: 4,709,046

[45] Date of Patent: Nov. 24, 1987

[54] ACYLMERCAPTOALKANOYL AND MERCAPTOALKANOYL SPIRO COMPOUNDS

[75] Inventor: John Krapcho, Somerset, N.J.

[73] Assignee: E. R. Squibb & Sons, Inc., Princeton, N.J.

[21] Appl. No.: 492,524

[22] Filed: May 9, 1983

[51] Int. Cl.$^4$ .............. C07D 491/113; C07D 495/10; A61K 31/40; A61K 31/44

[52] U.S. Cl. ........................ 548/409; 546/15

[58] Field of Search .................. 548/409; 546/15; 424/263, 274

[56] References Cited

U.S. PATENT DOCUMENTS 4,105,776  9/1978  Ondetti et al. ............... 424/274
4,311,697  1/1982  Krapcho ....................... 424/240
4,384,123  5/1983  Petrillo, Jr. .................. 548/409

OTHER PUBLICATIONS

Brunner et al., "Oral Angiotensin-Converting Enzyme Inhibitor . . . ", Ann. of Int. Med., vol. 90 pp. 19-23 (1979).

Aldigier et al., "Dose Dependency of Captopril . . . ," J. Cardiovasc. Pharmacol., vol. 3, No, 6, 1229-1235 (1981).

Primary Examiner—Mark L. Berch
Attorney, Agent, or Firm—Lawrence S. Levinson; Stephen B. Davis

[57] ABSTRACT

Spiro compounds of the formula

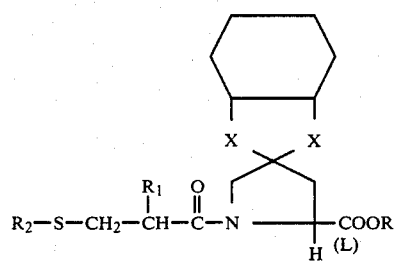

wherein X is oxygen or sulfur. These compounds possess antgiotensin converting enzyme inhibition activity and are thus useful as anti-hypertension agents.

13 Claims, No Drawings

ACYLMERCAPTOALKANOYL AND MERCAPTOALKANOYL SPIRO COMPOUNDS

BACKGROUND OF THE INVENTION

Ondetti et al. in U.S. Pat. No. 4,105,776 disclose that various acylmercaptoalkanoyl and mercaptoalkanoyl derivatives of proline, hydroxy substituted proline, and alkyl substituted proline possess angiotensin converting enzyme inhibition activity and thus are useful as anti-hypertension agents.

Krapcho in U.S. Pat. No. 4,311,697 disclose that various acylmercaptoalkanoyl and mercaptoalkanoyl derivatives of diether or dithioether substituted prolines and ketal or thioketal substituted prolines also possess angiotensin converting enzyme inhibition activity.

SUMMARY OF THE INVENTION

This invention is directed to new acylmercaptoalkanoyl and mercaptoalkanoyl spiro compounds of the formula

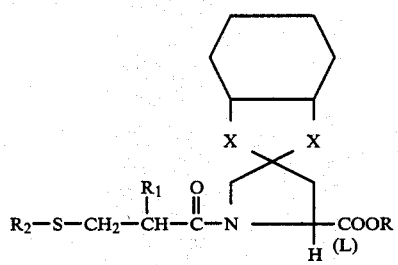

and pharmaceutically acceptable salts thereof.

R is hydrogen, lower alkyl, or a salt forming ion.

X is oxygen or sulfur.

$R_1$ is hydrogen, lower alkyl, or trifluoromethyl.

$R_2$ is hydrogen or

$R_3$ is lower alkyl,

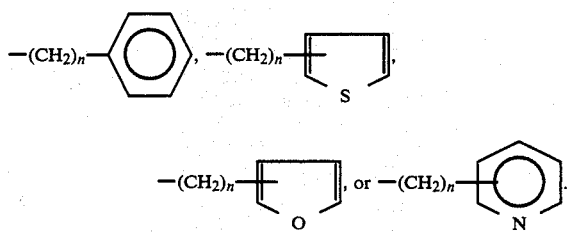

n is zero or an integer from 1 to 4.

DETAILED DESCRIPTION OF THE INVENTION

This invention in its broadest aspects relates to the substituted proline compounds of formula I above, to compositions containing such compounds and the method of using such compounds as anti-hypertensive agents.

The term lower alkyl represents straight or branched chain hydrocarbon radicals having up to seven carbons, for example, methyl, ethyl, propyl, isopropyl, butyl, isobutyl, t-butyl, pentyl, hexyl, heptyl, etc. The preferred lower alkyl groups are up to four carbons with methyl and ethyl being most preferred.

The symbols

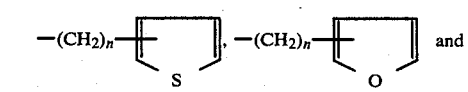

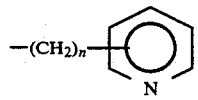

represent that the alkylene bridge is attached to an available carbon atom.

The compounds of formula I can be prepared as follows. An N-protected 4,4-dimethoxy substituted proline of the formula

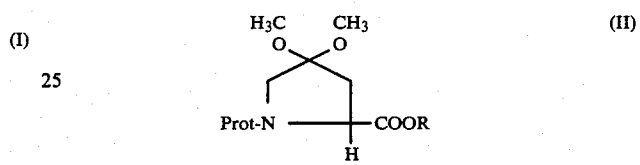

wherein Prot is a protecting group such as benzyloxycarbonyl, is reacted with a diol or dithiol of the formula

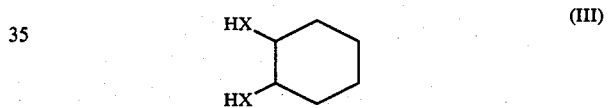

to give the N-protected proline of the formula

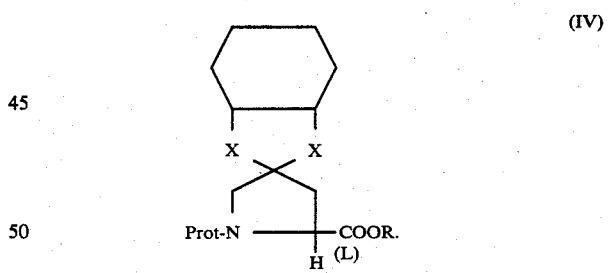

Removal of the N-protecting group, for example, by hydrogenation when X is oxygen and by hydrolysis when X is sulfur, yields the proline of the formula

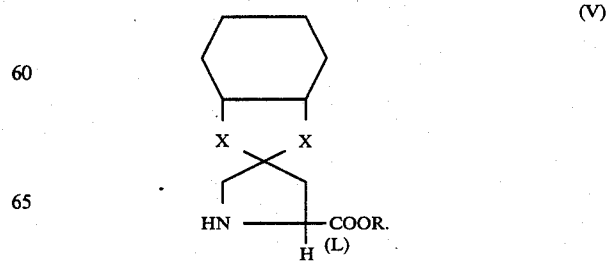

The proline of formula V is coupled with an acid or its chemical equivalent of the formula

to yield the acylmercaptoalkanoyl compound of the formula

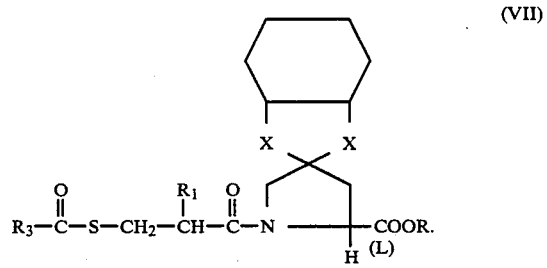

This reaction can be performed in the presence of a coupling agent such as dicyclohexylcarbodiimide or the like, or by conversion of the acid of formula VI to its mixed anhydride, symmetrical anhydride, acid halide, active ester, or by use of Woodward reagent K, N-ethoxycarbonyl-2-ethoxy-1,2-dihydroquinoline or the like. For a review of the methods of acylation see Methoden der Organishchen Chemie (Houben-Weyl), Vol. XV, part II, page 1 et seq. (1974). Preferably the said chloride of formual VI is reacted with the acid of formula V.

Hydrolysis or ammonolysis of the compound of formula VII yields the corresponding product of formula I wherein $R_2$ is hydrogen.

Also, the products of formula I wherein $R_2$ is hydrogen can be acylated with an acid halide, preferably the acid chloride, of the formula

to yield acylmercaptoalkanoyl products having other

groups.

The esters of formula I wherein R is lower alkyl can be obtained from the carboxylic acid compounds, i.e., wherein R is hydrogen, by conventional esterification procedures, e.g., by esterification with a diazoalkane such as diazomethane, 1-alkyl-3-p-tolyltriazine such as 1-n-butyl-3-p-tolyltriazine, or the like. The esters can also be obtained by treating the acid with an alcohol of the formula R—OH in the presence of a Lewis acid such as sulfuric acid, boron trifluoride, etc., at room temperature.

If the compounds of the formula I are obtained in the ester form they can be converted to the carboxylic acid by conventional means. For example, if R is t-butyl treatment with trifluoroacetic acid and anisole gives the carboxylic acid compound, i.e., R is hydrogen.

The compounds of formula I wherein $R_1$ is other than hydrogen contain an asymmetric center. These compounds can accordingly exist in stereoisomeric forms or as racemic mixtures thereof. The synthesis described below can utilize the racemate or one of the enantiomers as starting materials. When the racemic starting material is used in the synthesis, the stereoisomers obtained in the final product can be separated by conventional chromatographic or fractional crystallization procedures.

The diol or dithiol of formula III can be employed as the cis or trans isomer or as a mixture of cis and trans isomers and this configuration will be imparted to the product of formula I.

Preferably, if there is an asymmetric center in the acylmercaptoalkanoyl or mercaptoalkanoyl sidechain it is in the D-configuration.

The compounds of this invention form basic salts with various inorganic and organic bases which are also within the scope of the invention. Such salts include ammonium salts, alkali metal salts like lithium, sodium and potassium salts (which are preferred), alkaline earth metal salts like calcium and magnesium salts, salts with organic bases, e.g., dicyclohexylamine salt, 1-adamantanamine salt, benzathine, N-methyl-D-glucamine, hydrabamine salts, salts with amino acids like arginine, lysine and the like. The non-toxic, physiologically acceptable salts are preferred, although other salts are also useful, e.g., in isolating or purifying the product. The salts are formed using conventional techniques.

Preferred compounds of this invention are those of formula I wherein:

R is hydrogen or an alkali metal ion;
$R_1$ is methyl;
X is oxygen or sulfur, especially oxygen; and
$R_2$ is hydrogen,

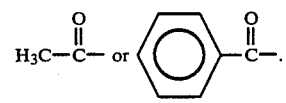

The compounds of formula I, and the pharmaceutically and physiologically acceptable salts thereof, are hypotensive agents. They inhibit the conversion of the decapeptide angiotensin I to angiotensin II and, therefore, are useful in reducing or relieving angiotensin related hypertension. The action of the enzyme renin on angiotensin, a pseudoglobulin in blood plasma, produces angiotensin I. Angiotensin I is converted by angiotensin converting enzyme (ACE) to angiotensin II. The latter is an active pressor substance which has been implicated as the causative agent in several forms of hypertension in various mammalian species, e.g., humans. The compounds of this invention intervene in the angiotensin→(renin)→angiotensin I→angiotensin II sequence by inhibiting angiotensin converting enzyme and reducing or eliminating the formation of the pressor substance angiotensin II. Thus by the administration of a composition containing one (or a combination) of the compounds of this invention, angiotensin dependent hypertension in a species of mammal (e.g., humans) suffering therefrom is alleviated. A single dose, or preferably two to four divided daily doses, provided on a basis of about 0.1 to 100 mg. per kilogram of body weight per day is appropriate to reduce blood pressure. The substance is preferably administered orally, but parenteral routes such as the subcutaneous, intramuscular, intravenous or intraperitoneal routes can also be employed.

The compounds of this invention can also be formulated in combination with a diuretic for the treatment of hypertension. A combination product comprising a compound of this invention and a diuretic can be administered in an effective amount which comprises a total daily dosage of about 30 to 600 mg., preferably about 30 to 330 mg. of a compound of this invention, and about 15 to 300 mg., preferably about 15 to 200 mg. of the diuretic, to a mammalian species in need thereof. Exemplary of the diuretics contemplated for use in combination with a compound of this invention are the thiazide diuretics, e.g., chlorothiazide, hydrochlorothiazide, flumethiazide, hydroflumethiazide, bendroflumethiazide, methyclothiazide, thrichlormethiazide, polythiazide or benzthiazide as well as ethacrynic acid, ticrynafen, chlorthalidone, furosemide, musolimine, bumetanide, triamterene, amiloride and spironolactone and salts of such compounds.

The compounds of formula I can be formulated for use in the reduction of blood pressure in compositions such as tablets, capsules or elixirs for oral administration, or in sterile solutions or suspensions for parenteral administration. About 10 to 500 mg. of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The following examples are illustrative of the invention. Temperatures are given in degrees centigrade.

EXAMPLE 1

[(3a,7a-trans),1'(S),5'S]-Hexahydro-1'-(3-mercapto-2-methyl-1-oxopropyl)spiro[1,3-benzodioxole-2,3'-pyrrolidine]-5'-carboxylic acid (a)

[(3a,7a-trans),5'S]-Hexahydro-1'-[(phenylmethoxy)carbonyl]spiro[1,3-benzodioxole-2,3'-pyrrolidine]-5'-carboxylic acid, methyl ester Interaction of N-carbobenzyloxy-4,4-dimethoxy-L-proline, methyl ester (8.4 g., 26 mmole, prepared as set forth in Example 3(a) of U.S. Pat. No. 4,311,697) and trans-1,2-cyclohexanediol (3.6 g., 31 mmole) in 400 ml. of refluxing toluene in the presence of 0.4 g. of p-toluenesulfonic acid for 45 minutes yields 10.1 g. of [(3a,7a-trans),5'S]-hexahydro-1'-[(phenylmethoxy)carbonyl]spiro[1,3-benzodioxole-2,3'-pyrrolidine]-5'-carboxylic acid, methyl ester as a yellow viscous oil. $R_f$ 0.64 (silica gel; ethyl acetate).

(b)

[(3a,7a-trans),5'S]-Hexahydro-1'-[(phenylmethoxy)carbonyl]spiro[1,3-benzodioxole-2,3'-pyrrolidine]-5'-carboxylic acid The methyl ester from part (a) (12.4 g., 32 mmole) is saponified with 20 ml. of 2N sodium hydroxide (40 mmole) in 80 ml. of methanol to give 10 g. of a reddish-orange sticky product.

This material is treated with 4.2 g. of 1-adamantanamine in 60 ml. of warm acetonitrile to give 12.3 g. of crude 1-adamantanamine salt; m.p. 208°–210° (dec.) [preceded by gradual darkening and sintering]. Trituration with 60 ml. of boiling acetonitrile and cooling gives 11.5 g. of [(3a,7a-trans),5'S]-hexahydro-1'-[(phenylmethoxy)carbonyl]spiro[1,3-benzodioxole-2,3'-pyrrolidine]-5'-carboxylic acid, 1-adamantanamine salt; m.p. 209°–211°. $[\alpha]_D^{25}$ −22° (c=1.0, methanol).

Anal. calc'd. for $C_{19}H_{23}NO_6 \cdot C_{10}H_{17}N \cdot 0.5\ H_2O$: C, 66.77; H, 7.92; N, 5.37. Found: C, 66.87; H, 7.85; N, 5.79.

This 1-adamantanamine salt is suspended in 40 ml. of ethyl acetate, stirred, and treated with 28 ml. of N hydrochloric acid. When two layers are obtained, they are separated and the aqueous phase is extracted with additional ethyl acetate (3×40 ml.). The combined organic layers are dried (MgSO4) and the solvent evaporated to give 7.3 g. of [(3a,7a-trans),5'S]-hexahydro-1'-[(phenylmethoxy)carbonyl]spiro[1,3-benzodioxole-2,3'-pyrrolidine]-5'-carboxylic acid as a yellow-orange sticky foam.

(c)

[(3a,7a-trans),5'S]-Hexahydro-spiro[1,3-benzodioxole-2,3'-pyrrolidine]-5'-carboxylic acid The product from part (b) (7.3 g., 20 mmole) is hydrogenated in 180 ml. of methanol:water (2:1) in the presence of 2 g. of 5% palladium on carbon catalyst to give 4.3 g. of crude [(3a,7a-trans),5'S]-hexahydro-spiro[1,3-benzodioxole-2,3'-pyrrodiline]-5'-carboxylic acid.

(d)

[(3a,7a-trans),1'(S),5'S]-Hexahydro-1'-[3-(acetylthio)-2-methyl-1-oxopropyl]spiro[1,3-benzodioxole-2,3'-pyrrolidine]-5'-carboxylic acid The crude [(3a,7a-trans),5'S]-hexahydro-spiro[1,3-benzodioxole-2,3'-pyrrolidine]-5'-carboxylic acid from part (c) (4.3 g., 19 mmole) is acylated with D-3-acetylthio-2-methylpropionyl chloride in 50 ml. of water in the presence of sodium carbonate at a pH of about 8.5 according to the procedure of Example 1 (e) of U.S. Pat. No. 4,311,697 to give 5.2 g. of crude produce as a yellow-orange sticky residue.

This crude product is converted to the dicyclohexylamine salt with 2.6 g. of dicyclohexylamine in 40 ml. of ethyl acetate. On seeding and rubbing, the crystalline salt precipitates to give 4.6 g. of dicyclohexylamine salt; m.p. 188°–190° (s. 180°). $[\alpha]_D^{25}$ −49° (c=1.0, ethanol). Trituration with 50 ml. of boiling acetonitrile and cooling gives 4.0 g. of nearly colorless solid [(3a,7a-trans),1'(S),5'S]-hexahydro-1'-[3-(acetylthio)-2-methyl-1-oxopropyl]spiro[1,3-benzodioxole-2,3'-pyrrolidine]-5'-carboxylic acid, dicyclohexylamine salt, m.p. 191°–193° (s. 188°).

$[\alpha]_D^{25}$ −51° (c=1.0, ethanol).

Anal. Calc'd. for $C_{17}H_{25}NO_6S \cdot C_{12}H_{23}N$: C, 63.01; H, 8.75; N, 5.07; S, 5.80. Found: C, 62.89; H, 8.75; N, 5.10; S, 5.97.

The dicyclohexylamine salt (3.9 g.) is converted to the free acid by suspending in 30 ml. of ethyl acetate and treating with 45 ml. of 10% potassium bisulfate and stirring until two layers are obtained. After separating, the aqueous phase is extracted with ethyl acetate (3×30 ml.), the organic layers are combined, dried (MgSO4) and the solvent evaporated to give 2.8 g. of colorless glass-like [(3a,7a-trans),1'(S),5'S]-hexahydro-1'-[3-(acetylthio)-2-methyl-1-oxopropyl]spiro[1,3-benzodioxole-2,3'-pyrrolidine]-5'-carboxylic acid. $[\alpha]_D^{25}$ −86° (c=1.0, ethanol). $R_f$ 0.42 (silica gel; dichloromethane/methanol/acetic acid; 90:5:5).

(e)

[(3a,7a-trans),1'(S),5'S]-Hexahydro-1'-(3-mercapto-2-methyl-1-oxopropyl)spiro[1,3-benzodioxole-2,3'-pyrrodiline]-5'-carboxylic acid The product from part (d) (2.7 g., 7.3 mmole) is hydrolyzed with 5 ml. of concentrated ammonia in 12 ml. of water over a period of one hour to yield 2.25 g. of amorphous solid. 2.1 g. of this material is taken up in 50 ml. of ethyl acetate (some crystallization occurs and dichloromethane is added to obtain solution), washed with water (3×15 ml.), dried (MgSO₄), and the solvents evaporated. The sticky residue is treated with 10 ml. of ether and swirled to give a hazy solution from which crystals begin to separate. Rapid crystallization is induced by rubbing and when essentially complete the mixture is diluted with 30 ml. of hexane, rubbed, and cooled. After three hours, the colorless solid is filtered under nitrogen, washed with hexane, and dried in vacuo to give 1.8 g. of [(3a,7a-trans),1'(S),5'S]-hexahydro-1'-(3-mercapto-2-methyl-1-oxopropyl)spiro[1,3-benzodioxole-2,3'-pyrrolidine]-5'-carboxylic acid; m.p. 147°–149° (s. 145°).

$[\alpha]_D^{25}$ −47° (c=1.0, ethanol). $R_f$ 0.40 (silica gel; dichloromethane/methanol/acetic acid; 90:5:5).

Anal. calc'd. for $C_{15}H_{23}NO_5S$: C, 54.69; H, 7.04; N, 4.25; S, 9.74. Found: C, 54.58; H, 7.21; N, 4.12; S, 9.75.

In a similar manner, by employing cis-1,2-cyclohexanediol in part (a), one can obtain [(3a,7a-cis),1'(S),5'S]-hexahydro-1'-(3-mercapto-2-methyl-1-oxopropyl)-spiro[1,3-benzodioxole-2,3'-pyrrolidine]-5'-carboxylic acid.

EXAMPLE 2

[1'(S),5'S]-Hexahydro-1'-(3-mercapto-2-methyl-1-oxopropyl)spiro[1,3benzodithiole-2,3'-pyrrolidine]-5'-carboxylic acid

(a)

(5'S)-Hexahydro-1'-[(phenylmethoxy)carbonyl]-spiro[1,3-benzodithiole-2,3'pyrrolidine]-5'-carboxylic acid, methyl ester Interaction of N-carbobenzyloxy-4,4-dimethoxy-L-proline, methyl ester and 1,2-cyclohexanedithiol according to the procedure of Example 1 (a) gives (5'S)-hexahydro-1'-[(phenylmethoxy)carbonyl]spiro[1,3-benzodithiole-2,3'-pyrrolidine]-5'-carboxylic acid, methyl ester.

(b)

(5'S)-Hexahydro-spiro[1,3-benzodithiole-2,3'-pyrrolidine]-5'-carboxylic acid, hydrobromide The product from part (a) is saponified by treatment with sodium hydroxide in aqueous methanol according to the procedure of Example 1(b). The resulting N-protected spiro carboxylic acid product is deprotected by hydrolysis with hydrogen bromide in acetic acid. Dilution with ether of the resulting solution after 10 minutes gives (5'S)-hexahydro-spiro[1,3-benzodithiole-2,3'-pyrrolidine]-5'-carboxylic acid, hydrobromide.

(c)

[1'(S),5'S]-Hexahydro-1'-[3-(acetylthio)-2-methyl-1-oxopropyl]spiro[1,3-benzodithiole-2,3'-pyrrolidine]-5'-carboxylic acid The product from part (b) is acylated with D-3-acetylthio-2-methylpropionyl chloride in water in the presence of sodium carbonate according to the procedure of Example 1(d) to give [1'(S),5'S]-hexahydro-1'-[3-(acetylthio)-2-methyl-1-oxopropyl]spiro[1,3-benzodithiole-2,3'-pyrrolidine]-5'-carboxylic acid.

(d)

[1'(S),5'S]-Hexahydro-1'-(3-mercapto-2-methyl-1-oxopropyl)spiro[1,3-benzodithiole-2,3'-pyrrolidine]-5'-carboxylic acid The product from part (c) is hydrolyzed with concentrated ammonia according to the procedure of Example 1(e) to yield [1'(S),5'S]-hexahydro-1'-(3-mercapto-2-methyl-1-oxopropyl)spiro[1,3-benzodithiole-2,3'-pyrrolidine]-5'-carboxylic acid.

EXAMPLES 3–15

Following the procedure of Examples 1 and 2, the spiro compound shown in Col. I is acylated with the acid chloride (or other activated form) shown in Col. II to give the acylmercaptoalkanoyl spiro product shown in Col. III. Hydrolysis with concentrated ammonia gives the mercaptoalkanoyl spiro product shown in Col. IV.

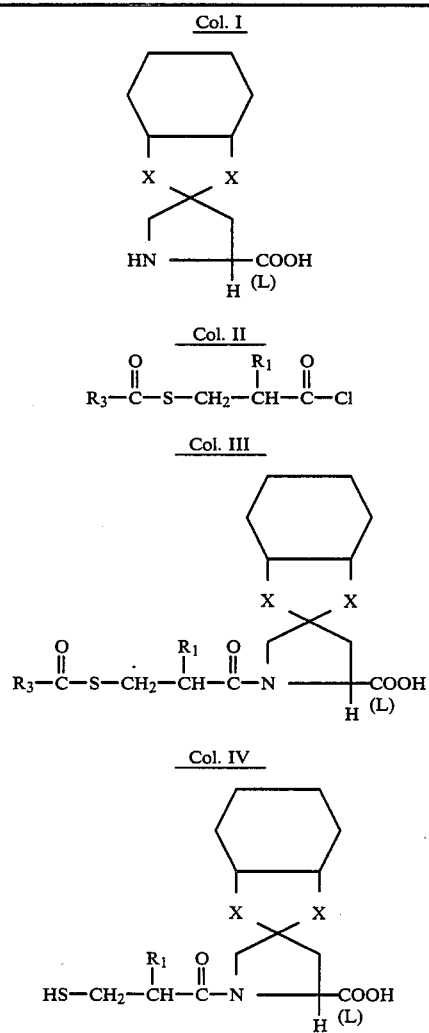

Example   X   R₁   R₃

-continued

| | | | |
|---|---|---|---|
| 3 | O | —CH₃ | 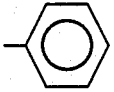 |
| 4 | S | —CH₃ | 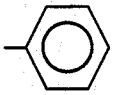 |
| 5 | O | —CH₃ | —CH₂—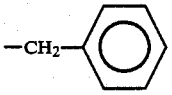 |
| 6 | S | —CH₃ | 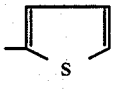 |
| 7 | O | —CH₃ | —CH₂—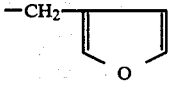 |
| 8 | O | —CH₃ | 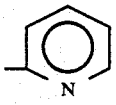 |
| 9 | S | —H | —CH₃ |
| 10 | O | —H | —CH₃ |
| 11 | S | —CF₃ | —CH₃ |
| 12 | O | —CF₃ | —C₂H₅ |
| 13 | O | —C₂H₅ | —CH₃ |
| 14 | S | —C(CH₃)₃ | —CH₃ |
| 15 | O | —CH₃ | —(CH₂)₂—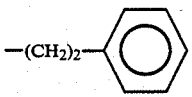 |

EXAMPLE 16

[(3a,7a-trans),1'(S),5'S]-Hexahydro-1'-(3-mercapto-2-methyl-1-oxopropyl)spiro[1,3-benzodioxole-2,3'-pyrrolidine]-5'-carboxylic acid, sodium salt An aqueous solution of the product from Example 1 is treated with sodium bicarbonate and lyophilized to give [(3a,7a-trans),1'(S),5'S]-hexahydro-1'-(3-mercapto-2-methyl-1-oxopropyl)spiro[1,3-benzodioxole-2,3'-pyrrolidine]-5'-carboxylic acid, sodium salt.

Similarly, by employing potassium bicarbonate in the above procedure, one obtains the corresponding salt.

In an analogous manner, the sodium or potassium salts of the product of Examples 2 to 15 can be prepared.

EXAMPLE 17

1000 tablets each containing the following ingredients:

| | |
|---|---|
| [(3a,7a-trans), 1'(S),5'S]-hexahydro-1'-(3-mercapto-2-methyl-1-oxopropyl)spiro[1,3-benzodioxole-2,3'-pyrrolidine]-5'-carboxylic acid, sodium salt | 100 mg. |
| Corn starch | 50 mg. |
| Gelatin | 7.5 mg. |
| Avicel (microcrystalline cellulose) | 25 mg. |
| Magnesium stearate | 2.5 mg. |
| | 185 mg. | are prepared from sufficient bulk quantities by mixing the [(3a,7a-trans),1'(S),5'S]-hexahydro-1'-(3-mercapto-2-methyl-1-oxopropyl)spiro[1,3-benzodioxole-2,3'-pyrrolidine]-5'-carboxylic acid sodium salt and corn starch and then adding an aqueous solution of gelatin. The mixture is dried and ground to a fine powder. The Avicel and then the magnesium stearate are added with granulation. This mixture is then compressed in a tablet press to form 1000 tablets each containing 100 mg. of active ingredient.

In a similar manner, tablets can be prepared containing 50 mg. of active ingredient.

The products of Examples 2 to 15 can be similarly formulated.

EXAMPLE 18

Two piece #1 gelatin capsules each containing 100 mg. of [1'(S),5'S]-hexahydro-1'-(3-mercapto-2-methyl-1-oxopropyl)spiro[1,3-benzodithiole-2,3'-pyrrolidine]-5'-carboxylic acid, sodium salt are filled with a mixture of the following ingredients:

| | |
|---|---|
| [1'(S),5'S]-hexahydro-1'-(3-mercapto-2-methyl-1-oxopropyl)spiro[1,3-benzodithiole-2,3'-pyrrolidine]-5'-carboxylic acid, sodium salt | 100 mg. |
| Magnesium stearate | 7 mg. |
| Lactose | 193 mg. |
| | 300 mg. |

In a similar manner, capsules can be prepared containing the products of any of Examples 1 and 3 to 15.

EXAMPLE 19

1000 tablets each containing the following ingredients:

| | |
|---|---|
| [(3a,7a-trans),1'(S),5'S]-hexahydro-1'-(3-mercapto-2-methyl-1-oxopropyl)spiro[1,3-benzodioxole-2,3'-pyrrolidine]-5'-carboxylic acid, sodium salt | 100 mg. |
| Avicel | 100 mg. |
| Hydrochlorothiazide | 12.5 mg. |
| Lactose | 113 mg. |
| Corn starch | 17.5 mg. |
| Stearic acid | 7 mg. |
| | 350 mg. | are produced from sufficient bulk quantities by slugging the [(3a,7a-trans),1'(S),5'S]-hexahydro-1'-(3-mercapto-2-methyl-1-oxopropyl)spiro[1,3-benzodioxole-2,3'-pyrrolidine]-5'-carboxylic acid, sodium salt, Avicel and a portion of the stearic acid. The slugs are ground and passed through a #2 screen, then mixed with the hydrochlorothiazide, lactose, corn starch, and remainder of the stearic acid. The mixture is compressed into 350 mg. capsule shaped tablets in a tablet press. The tablets are scored for dividing in half.

Similarly, the products of Examples 2 to 15 can be formulated according to this procedure.

EXAMPLE 20

An injectable solution is prepared as follows:

| | |
|---|---|
| [(3a,7a-cis),1'(S),5'(S)]-hexahydro-1'-(3-mercapto-2-methyl-1-oxopropyl)spiro[1,3-benzodioxole-2,3'-pyrrolidine]-5'-carboxylic acid, sodium salt | 500 g. |
| Methyl paraben | 5 g. |
| Propyl paraben | 1 g. |
| Sodium chloride | 25 g. |
| Water for injection | 5 l. |

The active substance, preservatives, and sodium chloride are dissolved in 3 liters of water for injection and then the volume is brought up to 5 liters. The solution is filtered through a sterile filter and asceptically filled into presterilized vials which are then closed with presterilized rubber closures. Each vial contains 5 ml. of solution in a concentration of 100 mg. of active ingredient per ml. of solution for injection.

In a similar manner, the products of Examples 1 to 16 can be formulated as described above.

What is claimed is:

1. A compound of the formula

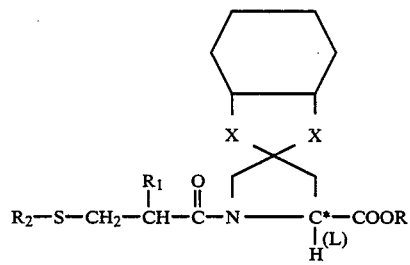

and a pharmaceutically acceptable salt thereof wherein:
X is oxygen or sulfur;
R is hydrogen, lower alkyl, or a pharmaceutically acceptable salt forming ion;
$R_1$ is hydrogen, lower alkyl, or trifluoromethyl;
$R_2$ is hydrogen or

$R_3$ is lower alkyl,

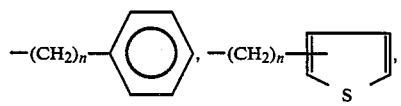

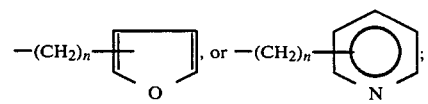

and n is zero or an integer from 1 to 4.

2. A compound of claim 1 wherein:
X is oxygen or sulfur;
R is hydrogen or an alkali metal salt ion;
$R_1$ is methyl; and
$R_2$ is hydrogen,

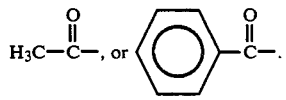

3. A compound of claim 2 wherein:
X is oxygen.

4. The compound of claim 3, [(3a,7a-trans),1'(S),5'S]-hexahydro-1'-(3-mercapto-2-methyl-1-oxopropyl)-spiro[1,3-benzodioxole-2,3'-pyrrolidine]-5'-carboxylic acid.

5. The compound of claim 3, [(3a,7a-trans),1'(S),5'S]-hexahydro-1'-[3-(acetylthio)-2-methyl-1-oxopropyl)-spiro[1,3-benzodioxole-2,3'-pyrrolidine]-5'-carboxylic acid.

6. The compound of claim 3, [(3a,7a-trans),1'(S),5'S]-hexahydro-1'-[3-(benzoylthio)-2-methyl-1-oxopropyl)-spiro[1,3-benzodioxole-2,3'-pyrrolidine]-5'-carboxylic acid.

7. The compound of claim 3, [(3a,7a-cis),1'(S),5'S]-hexahydro-1'-(3-mercapto-2-methyl-1-oxopropyl)-spiro[1,3-benzodioxole-2,3'-pyrrolidine]-5'-carboxylic acid.

8. The compound of claim 3, [(3a,7a-cis),1'(S),5'S]-hexahydro-1'-[3-(acetylthio)-2-methyl-1-oxopropyl]-spiro[1,3-benzodioxole-2,3'-pyrrolidine]-5'-carboxylic acid.

9. The compound of claim 3, [(3a,7a-cis),1'(S),5'S]-hexahydro-1'-[3-(benzoylthio)-2-methyl-1-oxopropyl]-spiro[1,3-benzodioxole-2,3'-pyrrolidine]-5'-carboxylic acid.

10. A compound of claim 2 wherein
X is sulfur.

11. The compound of claim 10, [1'(S),5'S]-hexahydro-1'-(3-mercapto-2-methyl-1-oxopropyl)spiro[1,3-benzodithiole-2,3'-pyrrolidine]-5'-carboxylic acid.

12. The compound of claim 10, [1'(S),5'(S)]-hexahydro-1'-[3-(acetylthio)-2-methyl-1-oxopropyl)spiro[1,3-benzodithiole-2,3'-pyrrolidine]-5'-carboxylic acid.

13. The compound of claim 10, [1'(S),5'S]-hexahydro-1'-[3-(benzoylthio)-2-methyl-1-oxopropyl]spiro[1,3-benzodithiole-2,3'-pyrrolidine]-5'-carboxylic acid.

* * * * *